US012702807B2

(12) United States Patent
Terry et al.

(10) Patent No.: US 12,702,807 B2
(45) Date of Patent: Aug. 11, 2026

(54) METHODS FOR MAKING MICRONEEDLES USING ADJUSTMENT OF COMPONENT SOLUBILITY IN CASTING FORMULATIONS

(71) Applicant: Georgia Tech Research Corporation, Atlanta, GA (US)

(72) Inventors: Richard N. Terry, Atlanta, GA (US); Mark R. Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1056 days.

(21) Appl. No.: 17/770,956

(22) PCT Filed: Oct. 22, 2020

(86) PCT No.: PCT/US2020/056939
§ 371 (c)(1),
(2) Date: Apr. 21, 2022

(87) PCT Pub. No.: WO2021/081260
PCT Pub. Date: Apr. 29, 2021

(65) Prior Publication Data

US 2022/0401715 A1 Dec. 22, 2022

Related U.S. Application Data

(60) Provisional application No. 62/933,739, filed on Nov. 11, 2019, provisional application No. 62/924,580, filed on Oct. 22, 2019.

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01)

(58) Field of Classification Search
CPC .............................................. A61M 2037/0053
See application file for complete search history.

(56) References Cited

U.S. PATENT DOCUMENTS 4,097,943 A 7/1978 O'Connell
6,007,836 A 12/1999 Denzer
(Continued)

FOREIGN PATENT DOCUMENTS

CN 103203072 A 7/2013
JP 2007089792 A 4/2007
(Continued)

OTHER PUBLICATIONS

Vora, L.K., et al., Novel nanosuspension-based dissolving microneedle arrays for transdermal delivery of a hydrophobic drug, Journal of Interdisciplinary Nanomedicine, vol. 3, No. 2 (2018), pp. 89-101. (Year: 2018).*

(Continued)

*Primary Examiner* — Matthew J Daniels
(74) *Attorney, Agent, or Firm* — Eversheds Sutherland (US) LLP

(57) ABSTRACT

Methods are provided that involve the intentional and controlled precipitation of a drug or active agent, or a reduction of solubility of a polymer or other film-forming component of a formulation, or a combination of both methods, to improve the processes for making microneedles or other objects by casting into molds and the resulting parts produced by casting. The selective reduction in solubility of formulation components solves many problems associated with the casting of polymer formulations into molds. The methods are preferably adapted for making microneedles of biodegradable polymer and drug composites, and may also
(Continued)

be used to produce other solid objects formed by casting into molds of compositions containing polymers and active agents.

30 Claims, 4 Drawing Sheets

(56) References Cited

U.S. PATENT DOCUMENTS

| | | | |
|---|---|---|---|
| 6,334,856 | B1 | 1/2002 | Allen et al. |
| 6,503,231 | B1 | 1/2003 | Prausnitz et al. |
| 6,611,707 | B1 | 8/2003 | Prausnitz et al. |
| 6,611,717 | B1 | 8/2003 | Clark et al. |
| 6,656,147 | B1 | 12/2003 | Gertsek et al. |
| 6,743,211 | B1 | 6/2004 | Prausnitz et al. |
| 6,945,952 | B2 | 9/2005 | Kwon |
| 7,182,747 | B2 | 2/2007 | Kwon |
| 7,211,062 | B2 | 5/2007 | Kwon |
| 7,226,439 | B2 | 6/2007 | Prausnitz et al. |
| 7,516,845 | B2 | 4/2009 | Lang et al. |
| 7,918,814 | B2 | 4/2011 | Prausnitz et al. |
| 8,062,573 | B2 | 11/2011 | Kwon |
| 8,101,114 | B2 | 1/2012 | Park et al. |
| 8,257,324 | B2 | 9/2012 | Prausnitz et al. |
| 8,419,708 | B2 | 4/2013 | Tokumoto et al. |
| 8,808,225 | B2 | 8/2014 | Prausnitz et al. |
| 9,302,903 | B2 | 4/2016 | Park et al. |
| 9,364,426 | B2 | 6/2016 | Gill et al. |
| 10,265,511 | B2 | 4/2019 | McAllister et al. |
| 10,828,478 | B2 | 11/2020 | McAllister et al. |
| 10,940,301 | B2 | 3/2021 | McAllister et al. |
| 2002/0192273 | A1 | 12/2002 | Buseman et al. |
| 2003/0187394 | A1 | 10/2003 | Wilkinson et al. |
| 2005/0228340 | A1 | 10/2005 | Cleary et al. |
| 2006/0084942 | A1 | 4/2006 | Kim et al. |
| 2007/0088248 | A1 | 4/2007 | Glenn et al. |
| 2008/0114298 | A1 | 5/2008 | Cantor et al. |
| 2008/0183144 | A1 | 7/2008 | Trautman et al. |
| 2008/0245764 | A1 * | 10/2008 | Pirk ...................... B81C 99/008 216/2 |
| 2009/0118662 | A1 | 5/2009 | Schnall |
| 2009/0182306 | A1 * | 7/2009 | Lee ......................... B29C 41/04 604/506 |
| 2010/0069726 | A1 | 3/2010 | Levinson |
| 2010/0256568 | A1 | 10/2010 | Frederickson et al. |
| 2010/0262081 | A1 | 10/2010 | Lee et al. |
| 2011/0152792 | A1 | 6/2011 | Takada |
| 2011/0245728 | A1 | 10/2011 | Eppstein et al. |
| 2012/0027810 | A1 | 2/2012 | Chen et al. |
| 2012/0041337 | A1 | 2/2012 | Ferguson et al. |
| 2012/0078189 | A1 | 3/2012 | Ogawa et al. |
| 2012/0109065 | A1 | 5/2012 | Backes |
| 2013/0006187 | A1 | 1/2013 | Kobayashi et al. |
| 2013/0023749 | A1 | 1/2013 | Afanaswelcz et al. |
| 2013/0158482 | A1 | 6/2013 | Davis et al. |
| 2014/0188041 | A1 | 7/2014 | Moore et al. |
| 2014/0276589 | A1 | 9/2014 | Bayramov et al. |
| 2016/0213908 | A1 | 7/2016 | McAllister et al. |
| 2017/0057124 | A1 * | 3/2017 | Wakamatsu ........... A61K 47/36 |
| 2018/0078498 | A1 * | 3/2018 | Petersson ............... A61K 31/59 |
| 2018/0193256 | A1 | 7/2018 | Kabata et al. |
| 2018/0333898 | A1 | 11/2018 | Francis et al. |
| 2019/0015651 | A1 | 1/2019 | Tadros et al. |
| 2020/0238065 | A1 | 7/2020 | Prausnitz et al. |

FOREIGN PATENT DOCUMENTS

| | | | | |
|---|---|---|---|---|
| JP | 2009039171 | A | 2/2009 | |
| JP | 2011224332 | A | 10/2011 | |
| JP | 2012196426 | A | 10/2012 | |
| JP | 2012200572 | A | 10/2012 | |
| JP | 2016074924 | A | 4/2013 | |
| KR | 100682534 | B1 | 2/2007 | |
| WO | 2010140760 | A2 | 12/2010 | |
| WO | 2013096026 | A1 | 6/2013 | |
| WO | WO-2014077242 | A1 * | 5/2014 | ............. B29C 39/24 |
| WO | 2017043627 | A1 | 3/2017 | |

OTHER PUBLICATIONS

Li, W., et al., Rapidly separable microneedle patch for the sustained release of a contraceptive, Nature Biomedical Engineering, vol. 2 (Mar. 2019), pp. 220-229. (Year: 2019).*

PCT International Search Report and Written Opinion for PCT Application No. PCT/US2020/056939 mailed Oct. 22, 2020 (16 pages).

* cited by examiner

METHODS FOR MAKING MICRONEEDLES USING ADJUSTMENT OF COMPONENT SOLUBILITY IN CASTING FORMULATIONS

CROSS-REFERENCE TO RELATED APPLICATIONS

This application claims priority to U.S. Provisional Patent Application No. 62/924,580, filed Oct. 22, 2019, and U.S. Provisional Patent Application No. 62/933,739, filed Nov. 11, 2019, which are incorporated herein by reference.

STATEMENT REGARDING FEDERALLY SPONSORED RESEARCH OR DEVELOPMENT

This invention was made with government support under grant number AID-0AA-A-15-00045 awarded by United States Agency for International Development. The U.S. government has certain rights in this invention.

BACKGROUND

The invention is generally in the field of formulations for casting and associated methods, particularly for making microneedles, for example, in arrays of microneedles formed of a polymer-drug composite.

Microneedles are micron-scale structures that can administer drugs in a minimally invasive manner. Microneedle patches having an array of microneedles that can be inserted into the skin, where they will either dissolve or detach from the rest of the microneedle patch when it is removed, leaving the agents to be delivered in the skin, are disclosed in WO 2019/075275 by Georgia Tech Research Corporation, which is incorporated herein by reference. This may be accomplished when the microneedles are fabricated from water-soluble polymer formulations. In this case, once the microneedle is inserted into the skin, the tip of the needle begins to dissolve and deposit its contents within the tissue. However, if the microneedle tip is fabricated from a non-water-soluble polymer formulation, this non-dissolvable tip will need to detach from the rest of the microneedle patch so as to remain implanted in tissue when the patch is removed. After the detached needle tips are deposited within the skin, they can begin to release their contents, often involving biodegradation of the microneedle tip materials. In this way, microneedle patches can deliver drugs or other active agents that release over time within the skin.

A desirable method of fabricating such a microneedle, or an array of such microneedles, is by casting a liquid formulation onto/into a mold containing an array of microneedle cavities. However, there remains a need for new and improved methods of casting microneedles, for example, to improve filling of mold cavities, reduce loss of drug to undesired or inoperable regions of the molded article, and aid in detachment of microneedle tips.

BRIEF SUMMARY

In one aspect, a method is provided for making a polymeric microneedle by casting. The method, according to some embodiments, includes (a) preparing a casting solution which comprises at least one organic solvent and a polymer and, optionally, a substance of interest, wherein the polymer and the substance of interest, if present, are fully dissolved in the casting solution; (b) (i) adding a nonsolvent for the polymer to the casting solution, and/or (ii) evaporating at least a portion of the at least one organic solvent, wherein the adding and/or evaporating are effective to reduce the effective molecular volume of the polymer in the casting solution; and (c) casting the casting solution in a mold for the microneedle. In some preferred embodiments, the at least one organic solvent includes two different organic solvents.

In a preferred embodiment, the casting solution comprise a substance of interest, wherein the adding a nonsolvent to the casting solution, and/or the evaporating at least a portion of the at least one organic solvent is/are effective to precipitate the substance of interest as a colloid or suspension in the casting solution.

In some embodiments, the step of evaporating at least a portion of the at least one organic solvent occurs before the casting solution is introduced into the mold. In some other embodiments, the step of the evaporating at least a portion of the at least one organic solvent occurs after the casting solution is introduced into the mold.

In some embodiments, the step of adding of the nonsolvent to the casting solution occurs before the casting solution is introduced into the mold.

The casting may include drying, centrifugation, and/or application of a vacuum to the casting solution in the mold.

The mold, which may be formed of any suitable material, may include one or more cavities each having a microneedle tip portion and a funnel portion. In preferred embodiments of the methods, the casting solution forms the microneedle tip portion, and the reduction of the effective molecular volume is effective to avoid formation of a polymeric film on the funnel portion.

In another aspect, a method is provided for making a microneedle, wherein the method includes: (a) preparing a casting solution which comprises at least one organic solvent and a polymer and a substance of interest, wherein the polymer and the substance of interest are fully dissolved in the casting solution; (b) (i) adding a nonsolvent to the casting solution, and/or (ii) evaporating at least a portion of the at least one organic solvent, wherein the adding and/or evaporating is/are effective to precipitate the substance of interest as a colloid or suspension in the casting solution; and (c) casting the casting solution in a mold for the microneedle. In some preferred embodiments, the at least one organic solvent includes two different organic solvents.

In some embodiments of this method, the step of evaporating at least a portion of the at least one organic solvent occurs before the casting solution is introduced into the mold. In some other embodiments, the step of the evaporating at least a portion of the at least one organic solvent occurs after the casting solution is introduced into the mold.

In some embodiments, the step of adding of the nonsolvent to the casting solution occurs before the casting solution is introduced into the mold.

The casting may include drying, centrifugation, and/or application of a vacuum to the casting solution in the mold.

The mold, which may be formed of any suitable material, may include one or more cavities each having a microneedle tip portion and a funnel portion. In preferred embodiments of this method, the casting solution forms the microneedle tip portion, and the reduction of the effective molecular volume is effective to avoid formation of a polymeric film on the funnel portion.

In some preferred embodiments of any of these methods, the mold is formed of silicone or another elastomer.

In another aspect, a microneedle array is provided that is configured for administering a substance of interest into a patient's biological tissue. In some embodiments, the microneedle array is fabricated by a process that includes one of the methods described above. In some embodiments, the microneedle array includes (a) a base; and (b) two or more microneedles extending from the base, wherein each of the two or more microneedles has (i) a tip portion, which is formed predominantly of a first material which comprises a polymer and a substance of interest, and (ii) a funnel portion, which is formed predominantly of a second material, the funnel portion extending between the base and the tip portion, wherein the first material is formed from a first cast, the second material is formed from a second cast, and an interface of the first material and the second material is flat. In some preferred embodiments, the polymer comprises PLGA, PLA, or another biodegradable polymer.

The funnel portion may include a water-soluble matrix material, and the two or more solid microneedles may be constructed to penetrate into the patient's biological tissue under compression, where the tip portions are configured to separate from the funnel portions upon at least partial dissolution of the water-soluble matrix material in the funnel portions. The funnel portion may further include an effervescent material.

The substance of interest may include an active pharmaceutical ingredient, such as a contraceptive hormone.

The substance of interest may be in the form of particles from 1 nm to 1 μm, which are dispersed in the polymer. For example, the particles may be from 10 nn to 900 nm, from 50 nm to 800 nm, from 100 nm to 1 μm, or from 500 nm to 1 μm. The particles may be formed in the microneedle by casting a polymer solution in which the substance of interest has been precipitated as a colloid or suspension prior to casting.

In still another aspect, a method is provided for administering a substance of interest to a patient. The method includes (a) inserting into a biological tissue of the patient, e.g., the patient's skin, the microneedles of an array of microneedles as described above; (b) separating the inserted microneedle tip portions from the funnel portions; and (c) releasing the substance of interest, from the separated microneedle tip portions, into the biological tissue. The separating may include dissolution of a water-soluble polymer forming part of the microneedle array, e.g., forming the funnel portion.

DETAILED DESCRIPTION

Improved methods that include casting solvent-based formulations into molds, particularly silicone or other elastomeric molds, have been developed, which methods reduce or eliminate problems associated with conventional casting methods.

These improved methods can be applied to fabricating microneedles or other fine medical devices or other three dimensional articles. In a preferred embodiment, the methods are used to make microneedle arrays for microneedle patches that are configured to administer therapeutic or prophylactic agents into skin.

Identification of Problems to be Solved

Figure 2:
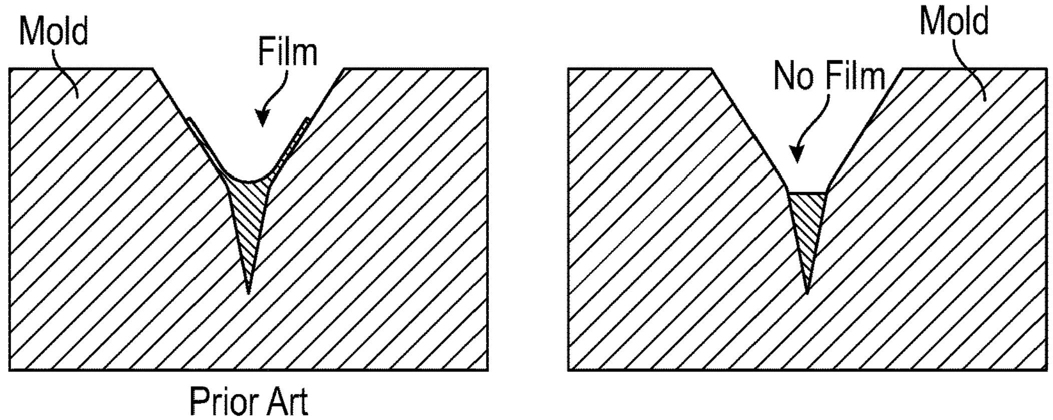
FIG. 2 is a cross-sectional view comparing microneedle tips formed in a mold, where the left view illustrates poor tip formation due to film forming in the upper regions of the mold (obtained using conventional processes) and the right view illustrates good tip formation where the cast formulation has migrated into the tip of the mold (obtained using processes described herein).

One common method of fabricating a microneedle patch is by casting a liquid formulation onto a silicone mold containing an array of microneedle cavities. Once on the mold, the formulation is manipulated into the microneedle cavities by use of a variety of methods, including vacuum suction, centrifugation and pressure. These processes remove or displace the air trapped beneath the liquid formulation, allowing the liquid to fill the fine microneedle tips of the mold. Once the formulation has filled the microneedle cavities the solvents in the formulation are evaporated, leaving behind a solid formulation that forms the needle tips. One problem associated with this microneedle casting method is that the solids of the formulation tend to accumulate at the interface with the silicone mold (or mold made of other materials) due to the swelling of silicone by the solvents and the diffusion of solvents into the silicone mold. This can produce a film of material where the formulation contacts the mold, rather than having all the solid material migrate toward the tip portion of the microneedle where it is needed. The result is a concave center in the microneedle tips and a film of the formulation in the upper regions of the mold, where it is not desired. See FIG. 2, left side. This problem is greatest when using formulation solvents that have the greatest swelling effect on silicone, and least when using aqueous formulations, which are somewhat repelled by the hydrophobic silicone surfaces.

The film that forms in a silicone microneedle mold above the tip of a solid formulation after casting is problematic because this film can prevent the detachment of the needle tip beneath the skin after insertion when polymers that are not water soluble are used. Microneedles composed of biodegradable polymers, for example, can be covered with a water-soluble backing material that forms the primary structure of the microneedle patch. Once the patch is inserted into the skin, the tissue fluid contacts the water-soluble backing, causing it to dissolve and release the biodegradable polymer tips, depositing them in the skin. If a film of biodegradable polymer exists in the region above the needle tip where the water-soluble polymer should reside, this water-insoluble film can block the migration of interstitial fluid into the water-soluble backing, preventing detachment of the tips. This can cause some of the microneedle tips to remain with the patch when it is removed, reducing the quantity of the drug or active agent that was intended to be delivered to the skin by the microneedle tips. When a drug/polymer film forms in the mold cavity above the microneedle tips it reduces the amount of active agent in the tip, thereby reducing the amount of drug or active agent delivered to the skin by the tips.

Another problem encountered in the fabrication of microneedles is the difficulty in casting formulations containing suspended particles of active agents. When insoluble particles must be suspended into microneedle casting formulations, it is difficult to produce stable suspensions of sufficiently small particles that they do not agglomerate and collect in the upper regions of a mold during casting. Another problem with suspended-particle formulations is that the particles tend to settle, causing them to concentrate in the dispensing device before the casting can be complete and particles will also settle in the storage container if not stirred. The settling of drug particles can cause drug concentration variations within a given lot of cast microneedles. These are commonly observed limitations to the use of formulations in which the active agents have been suspended from a powder, and thus there is a need for an improved method of suspending insoluble particles of active agents in castable polymer/drug formulations. By the methods of this invention, active agents can be precipitated in situ directly within a castable formulation, creating a stable colloidal suspension of the active agent that has a much smaller particle size than can typically be achieved by suspension of dry particles of the same active agent. The created colloidal suspensions are much less likely to settle from solution, adhere to silicone mold surfaces, and agglomerate into particle clusters. The smaller particle size of in situ-formed colloidal particles also allows them to fill the deeper regions of sharp tip cavities, producing much higher agent concentrations in the tip than are often achieved with dry powder suspensions of the same active agent.

Swelling of the silicone mold material is another problem associated with casting solvent-based formulations containing soluble active agents into silicone or other polymeric molds. The solvents used to dissolve the polymer and drug can and generally do diffuse into and swell the silicone mold. During swelling, drugs that are dissolved in the formulation can be carried into silicone by the flux of diffusing solvent, reducing the amount of active agent that remains in the formed microneedle tips. The flux of solvent into the mold also allows the ends of soluble polymer chains to migrate a short distance into the mold surface, leaving polymer film wherever polymer solutions contact the mold and reducing polymer migration into the tip where it is needed. Polymer that is deposited in this manner will also trap and deposit the active agents, reducing their concentration in the tips.

Thus, there is an important need for new methods of casting microneedles that reduce or eliminate the film that forms on the surfaces of the microneedle molds to improve the filling and detachment of microneedle tips and reduce the amount of drug not deposited in the mold cavities where it is needed. There is also a need for improved casting formulations that contain a stable suspensions of insoluble active agents in order to reduce soluble drug loss during mold swelling. Although directed towards casting of microneedles, these same needs exist in the casting of many other types of devices into molds of any material that swells in the solvents of the cast formulation.

Improvements and Solutions to the Identified Problems

The presently disclosed methods address one or more of the foregoing needs for a wide range of castable devices and materials.

It has been found by experimentation that when organic solvents are used to cast polymers into, for example, silicone molds, the air interface above the deposited film is usually convex and conical, not flat as desired. This has been attributed to a combination of the solvent flux into the silicone material of the mold as it swells and evaporation of solvent from the formulation after casting, both of which leave the polymer deposited on the entire contact surface of the silicone. The phenomenon of polymer deposition by mold swelling can be likened to filtration, where the solvent is pulled away from the solution, leaving behind the solids, which cannot follow it. A principal part of the present methods is the discovery that reducing the polymer solubility in a formulation to be cast reduced the amount of film that forms on the silicone mold surfaces. This can be attributed to two things: The reduction of mold swelling by increasing the percentage of polymer nonsolvents that are lower swelling in the formulation and the reduction of the polymer conformation in solution when its solubility is reduced by evaporation of a good solvent or addition of poor or nonsolvent. The polymer conformation in solution can be defined as the average distance from one end of the polymer chain to the other, as the randomly coiled polymer exists in solution. The intermolecular interactions between polymer chain segments and coordinated solvent molecules have an associated energy of interaction, which can be positive or negative. For a good solvent, interactions between polymer segments and solvent molecules are energetically favorable, and will cause polymer coils to expand. For a poor solvent, polymer-polymer self-interactions are preferred, and the polymer coils will contract. The quality of the solvent depends on both the chemical compositions of the polymer and solvent molecules and the solution temperature. Reducing the polymer conformation in solution by bringing the polymer close to the point of precipitation, either by evaporating a good solvent or adding a poor solvent, reduces the polymer molecules' interaction with the mold surface, allowing the polymer molecules to be more easily forced down into the fine cavities of a mold by, for example, centrifugation or suction. This important discovery allowed the creation of improved methods for making microneedles and improved the quality of microneedles by better packing of the mold cavities. These methods enable one to create substantially flatter (better) interfaces between the tip and funnel portions of the microneedles. See FIG. 2, right side.

Figure 7:
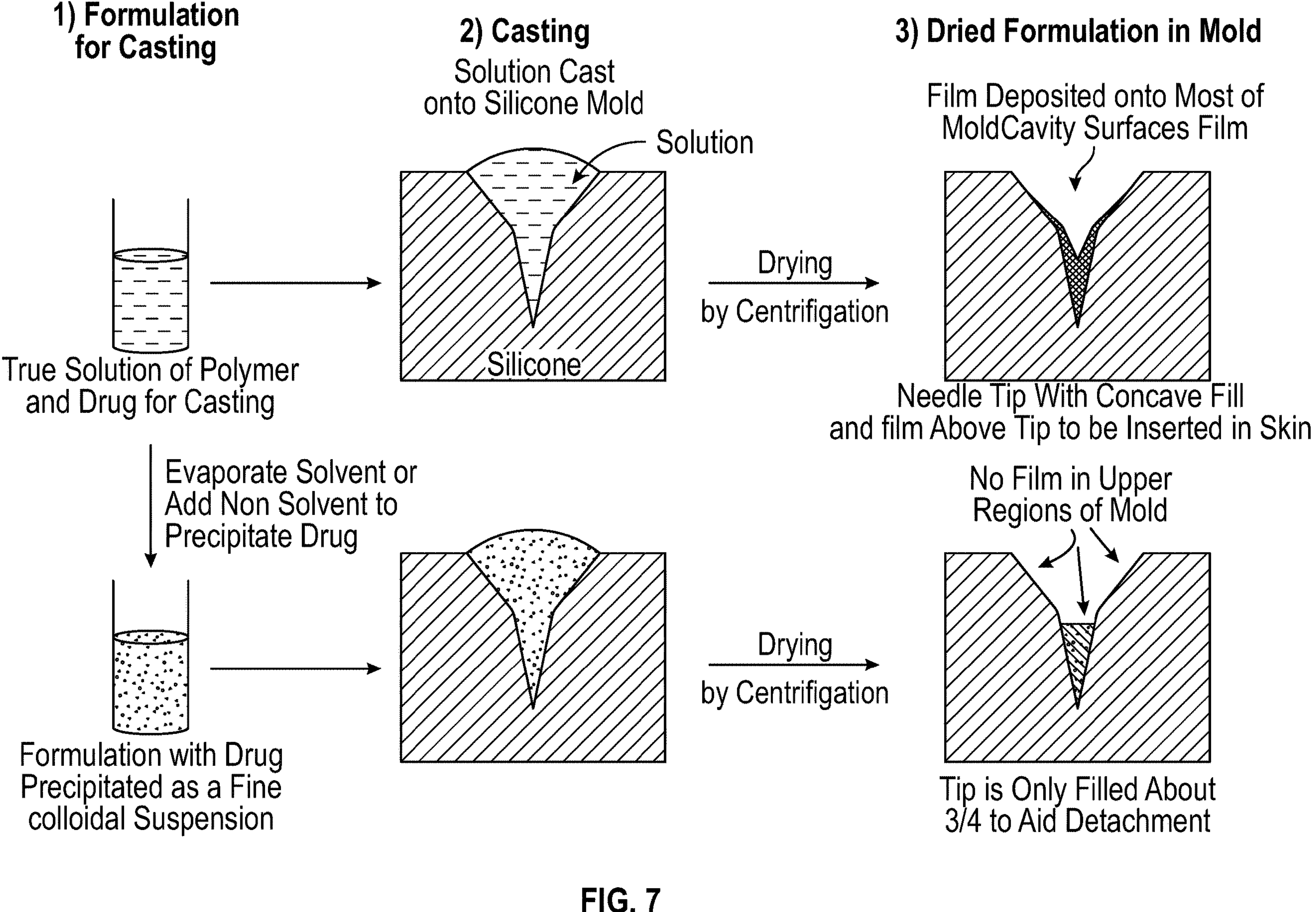
FIG. 7 is a schematic illustration comparing a conventional process versus one embodiment of the presently disclosed processes for forming a microneedle tip in a mold by casting.

FIG. 7 also illustrates an example of the improved results obtainable with the presently described methods, showing a better microneedle tip structure obtainable, with no precipitate on the funnel portion of the mold.

The improvements are accomplished by selectively reducing the solubility of the drug or active agent and/or the polymer comprising the formulation to be cast into a mold. The selective reduction in solubility of formulation components may seem counter-intuitive, but solves many problems associated with the casting of polymer formulations into molds. That is, the improved methods described herein involve the unpredictable solution of precipitation or reduction in solubility of one or more solutes within a castable liquid formulation to favorably alter the casting properties and/or improve the quality of solid objects made from casting said formulations.

Accordingly, the presently disclosed methods advantageously can be effective to (i) reduce or eliminate the formation of film above articles cast from solvent in silicone molds or molds made of other materials, improving the detachment of microneedles made from water-insoluble materials; (ii) improve the loading of active agents and polymer into the cavities of the molds to produce high quality parts; and (iii) increase the quantity of active agent that can be delivered to molds by the casting of a polymer formulation.

In general, the articles and methods described herein involve the intentional and controlled precipitation of a drug or active agent in a casting formulation, or a reduction of solubility of a polymer or other film-forming component of the formulation, or a combination of both methods, to produce a better casting fluid formulation prior to the fluid formulation being transformed into the solidified structure defined by the mold, e.g., prior to completion of casting and drying. That is, the formulation is able to improve the processes for making microneedles or other devices by casting into molds, by increasing the amount of active agent that is concentrated in the desired areas of the mold (e.g., the tip portion) and to thereby improve the quality of the resulting structures produced by the casting/molding.

The methods described herein employ new casting formulations that pack better into the microneedle tips or other fine details of silicone or other casting molds because they are less adherent to the mold surfaces and less likely to precipitate at the mold surfaces. Such new formulations have been made and demonstrated in microneedle molds to reduce the amount of film adhered to the mold above the needle tip, reduce the concavity of the cast microneedle tips, and increase the amount of drug or active agent in the microneedle tip. This beneficially improves the strength and quality of cast microneedles and ultimately can increase the concentration of drug or active agent delivered to the skin from the microneedle.

In various embodiments of the method, the solute that precipitates in the casting solution, e.g., prior to casting, can be drug or polymer, and the mechanism can be addition of nonsolvent and/or evaporation of good solvent in both cases. And furthermore, it need not involve a drug and a polymer, but could involve any pair of solutes, and can even involve just one solute. In the following description and examples, the methods may be associated with not precipitating a second solute, but the presence of a second solute is not required.

The precipitating solute in the casting solution, e.g., prior to casting, may be partially or fully precipitated (i.e., some could remain dissolved, and in general that would be the case).

Methods

In some embodiments, the methods include reducing the solubility of a polymeric component of a formulation to improve the casting properties and resulting articles cast from the formulation. In this method, the polymer has its solubility reduced to near the point of precipitation by (a) the evaporation of a good solvent for the polymer from a solution comprising a combination of at least one non-solvent for the polymer and the good solvent for the polymer, or (b) the addition of a non-solvent for the polymer to a solution of the polymer. In method (b), the effective solvent is evaporated after casting, rather than before casting, causing the polymer precipitation to occur directly within the mold cavities after casting as the volatile solvent within the cast formulation evaporates. Reducing the polymer solubility to a point just before precipitation reduces the polymer conformation in the casting solution, which reduces the polymer's interaction with the silicone mold surface, resulting in less polymer adhesion to the mold or localization near the mold surface, better packing into the area of the mold where the formulation is desired and little or no polymer film formation above where the polymer fills the mold cavity. Precipitating the polymer directly within the mold cavities after casting also reduces the polymer's ability to interact with the mold to form unwanted film. Here, the term "effective solvent for the polymer" refers to a solvent for the selected polymer in which the polymer is readily/fully soluble. The "non-solvent for the polymer" includes solvents in which the polymer is insoluble or only poorly soluble.

Accordingly, in one aspect of the invention, the method includes (a) preparing a casting solution which comprises at least one organic solvent and a polymer and, optionally, a substance of interest, wherein the polymer and the substance of interest, if present, are fully dissolved in the casting solution; (b) (i) adding a nonsolvent for the polymer to the casting solution, and/or (ii) evaporating at least a portion of the at least one organic solvent, wherein the adding and/or evaporating are effective to reduce the effective molecular volume of the polymer in the casting solution; and (c) casting the casting solution in a mold for the microneedle.

As used herein, the phrase "reduce the effective molecular volume of the polymer" refers to changing the polymer conformation so that it occupies less space, e.g., it has a smaller effective molecular size, hydrodynamic radius or radius of gyration. When changing the solvent composition to reduce the effective molecular volume, the change in solvent can be to make the solvent a theta solvent, which reduces the effective molecular volume of the polymer. The effective molecular volume of the polymer gets smaller when the concentration of the polymer is close to the solubility limit of the polymer in the solvent system, e.g., when the polymer concentration comes to within 10%, more preferably within 5% or as close as to within 1% to 2% of the polymer solubility limit.

Evidence of a reduction of effective molecular volume can be obtained by the visual observation of an increase in opacity of the solution in which the polymer is dissolved or measurement techniques including static light scattering, dynamic light scattering or other experimental, theoretical and computational methods known in the art. Measurement of polymer concentration can be done by optical spectroscopy, refractometry, chromatography, viscosity, density and other methods known in the art. Determination of the solubility limit of a polymer in a solvent system can be determined by measuring the concentration of the polymer of a saturated solution (e.g., with solid polymer in equilibrium with dissolved polymer), among other experimental, theoretical and computational methods known in the art.

As used herein, the term "precipitation" means the process of a solvent coming out of solution and forming a new phase, typically a solid phase, whether crystalline or amorphous, whether particulate or film geometry.

In some embodiments, the methods include precipitating a non-polymeric solute, such as a drug or active agent, within a formulation by the evaporation of a good solvent for the solute from a solution that includes a combination of at least one non-solvent (also to include poor solvents for the solute) for the solute and the good solvent for the solute. In a preferred embodiment, the drug is dissolved in a polymer solution containing the good solvent for the drug and non-solvent for the drug, with the good solvent having a faster evaporation rate, wherein the drug is precipitated as a fine colloidal suspension within the polymer solution by the evaporation of the good solvent for the drug. Then, the formulation with the precipitated drug is cast into the mold, e.g., silicone microneedle molds. See FIG. 3. Here, the good solvent is one in which a compound (e.g., the drug or active agent) has a solubility that is higher than its solubility in a non-solvent. A non-solvent does not necessarily have zero solubility of the compound, but must have a solubility that is very low, and much lower than the effective solvent, such that precipitation of the compound occurs upon evaporation of the good solvent. As a non-limiting example, the solubility for a compound in an good solvent is at least an order of magnitude higher than its solubility in the non-solvent.

The present methods are effective to improve the amount of drug or active agent delivered to the fine details of an intricate mold. In a preferred embodiment, the drug is delivered to the tips of a microneedle mold during fabrication. This is also accomplished by reducing the amount of the formulation that adheres to the silicone mold. By creating a formulation with reduced solvent swelling of the mold, improved migration of polymer/drug into the mold tip, and reduced film deposited above the tip, the amount of drug lost by migration into the mold and in the film above the tip is minimized and the amount of the formulation with active agent deposited in the microneedles tips is maximized.

In some embodiments, methods are provided for producing a fine colloidal suspension of a drug or active agent within a castable formulation by the in situ precipitation of an active agent within a formulation by evaporation of an effective solvent for the drug/agent, or by titration of the formulation with a non-solvent for the drug/agent. These methods are advantageous over conventional methods of suspending particles in formulations because they produce higher concentrations (i.e., higher number of particles per volume) of smaller-sized particles in suspension that are less likely to settle and/or agglomerate within the formulation compared to larger suspended particles. Suspended or colloidal particles are also less adherent to the silicone mold and are therefore more readily concentrated into the microneedle tip portions of a mold.

Using the casting methods described herein, microneedles can be produced that can increase the amount of drug or active agent that is delivered into the skin. This is accomplished by minimizing the film deposited on the mold above the tip, thereby maximizing the amount of drug/active agent in the microneedle tips and aiding in the complete detachment and delivery into the skin of the microneedle tips, and also by creating higher concentration drug/active agent suspensions in the formulations used to cast the microneedles.

The present methods may be used to produce a polymeric article by casting, where the addition of a non-solvent before the solution is cast into an elastomeric mold is used to reduce the solubility of a polymeric component of the formulation to reduce its interaction with the mold, resulting in better packing of the formulation into the mold. The mold can be made from silicone elastomer. In a preferred embodiment, the polymeric article is a microneedle, or at least a portion thereof, such as a microneedle tip.

Figure 3:
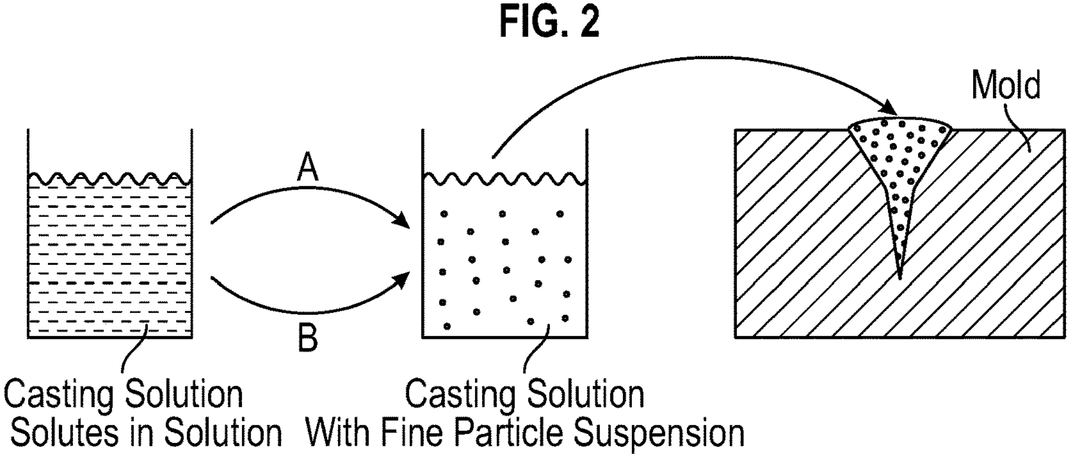
FIG. 3 illustrates two embodiments of adjusting a casting liquid for forming a microneedle tip as described herein.

In some embodiments, the methods are used to prepare a polymer-drug composite device fabricated by casting a polymer solution in which the drug has been precipitated, for example as a colloid, by the evaporation of an effective solvent for the drug from the formulation before casting, which is route A in the process shown in FIG. 3. In such embodiments, the polymer and the drug could be any pair of molecules with different solubility characteristics. The polymer-drug composite device may be a microneedle array, for example, as part of a microneedle patch.

In some other embodiments, the methods are used to prepare a polymer-drug composite device fabricated by casting a polymer solution in which the drug has been precipitated, for example as a colloid, by the addition of a non-solvent for the drug to the formulation before casting, which is route B in the process shown in FIG. 3. The polymer-drug composite device may be a microneedle array, for example, as part of a microneedle patch.

In still some other embodiments, a combination of (i) evaporation of an effective solvent for the drug from the formulation, and (ii) addition of a non-solvent for the drug to the formulation, is used to precipitate the drug before casting.

With any of these methods, the microneedle patch produced may be composed of a biodegradable polymer and at least one drug or active agent, such as a contraceptive hormone.

In some embodiments, a process is provided for making a microneedle or other objects in a mold, wherein the process includes casting a liquid onto/into a mold (such as a mold comprising one or more cavities in the shape of a microneedle), wherein the liquid comprises at least two solvents that have at least one solute dissolved therein and at least one solute that is precipitated in the solvent. The liquid thus can be both a solution and a suspension. In a preferred embodiment, the precipitate is a fine colloidal suspension, for example, that does not settle appreciably during the process of making the microneedle or other object. One solute may be a drug or other active agent, and another solute may be a polymer, such as a biodegradable polymer. Other solutes and polymers may be included. The precipitated solute in the cast liquid may be the drug or the polymer.

In some embodiments, a process is provided for making a microneedle or other objects in a mold, wherein the process includes the steps of (i) forming a solution comprising one or more solutes and at least two solvents, (ii) preferentially removing part of one or more of the solvents (for example by evaporation), but not all of the solvents, in an amount effective to preferentially precipitate, or in the case of polymers reduce the solubility of, at least one, but not all, of the solutes, wherein the precipitating solute(s) are more soluble in the preferentially removed solvent(s) than in the non-preferentially removed solvent(s), (iii) casting or otherwise applying the suspension onto/into a mold, and (iv) removing the remaining solvent(s) to form a microneedle, an array of microneedles, or another object comprised of the solutes.

In some embodiments, a process is provided for making a microneedle or other objects in a mold, wherein the process includes the steps of (i) forming a solution containing at least two solutes and at least two solvents, (ii) casting or otherwise applying the solution onto/into a mold, (iii) preferentially removing a part of one or more solvents (for example by evaporation), but not all of the solvents, in an amount effective to preferentially precipitate at least one, but not all, of the solutes, wherein the precipitating solute(s) are more soluble in the preferentially removed solvent(s) than in the non-preferentially removed solvent(s), and (iv) removing the remaining solvent(s) to form a microneedle, an array of microneedles, or another object comprised of the solutes. This is shown by route A in the process shown in FIG. 4.

In the foregoing methods, the at least two solutes are different substances from one another. For example, one solute may be a drug, which may ultimately become a dispersed phase in the solid microneedle, and a second solute may be a polymer, which may ultimately become a continuous phase (matrix material) in which the drug is dispersed in the solid microneedle.

Figure 4:
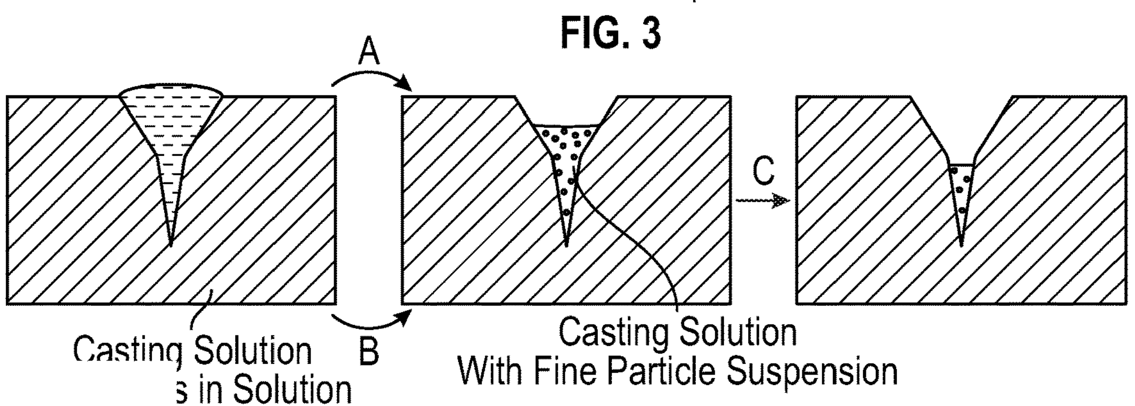
FIG. 4 illustrates an embodiment of adjusting a casting liquid for forming a microneedle tip as described herein.

In a variation of these methods illustrated in FIGS. 3-4, the casting solution comprises only a single solute. The single solute may be, for example, a polymer.

In the foregoing methods, the at least two solvents also are different substances from one another. For example, they may be different organic liquids, or an aqueous liquid and an organic liquid. The solvents are selected for their relative solubilities with respect to the solutes and solubility with one another, as described herein.

In some embodiments, a formulation comprising a polymer and a drug that has good solubility tolerance to water are dissolved in a solvent system containing a strong, volatile solvent and a low volatility solvent, forming a true solution of all ingredients, i.e., the solutes are fully dissolved in the solvent. Water, a strong non-solvent for the polymer, is then gradually added to the formulation until the solution turns hazy, indicating that the polymer, which was less tolerant of water than the drug, is close to precipitating from solution and exists in a tighter polymer conformation within the formulation. The solution turns hazy at the point in which the polymer conformation in solution becomes tight enough to reflect light, but the polymer has not yet precipitated from solution. In this embodiment, the volatile solvent is designed to evaporate quickly from the mold after casting, which causes the polymer, already near its limit of solubility in the solution, to quickly precipitate within the mold. It is hypothesized that because of its tight polymer conformation, the polymer has little ability to interact with the mold surfaces, particularly a porous mold surface, such as a silicone surface, to form a film. After casting, the molds are placed in a centrifuge, for example, which is then used to pack the polymer/drug composite into the tips of the microneedle cavities as it dries the formulation, leaving little or no polymer film adhered to the mold above the filled tips. The resulting microneedle tips produced by this method have essentially no film adhered to the silicone above the tips, and the tips display very little of the concavity that is typically seen when casting true polymer solutions, which leave polymer/drug film in the upper regions of the mold.

Microneedles and Other Cast Structures

In another aspect, microneedles are provided which have a tip portion and a funnel portion, where the interface of the material predominantly in the tip portion and the material predominantly in the funnel portion is flat. As used here, the term "flat" means the interface is substantially flat or planar, for example, when viewed at the scale illustrated in FIG. 6B. That is, the material predominantly in the tip portion does not also exist as a thin film that extends along the edges of the device into the funnel portion. The tip portion may be made of non-water soluble material (that may be degradable in water) wherein the tip portion is configured to separate from the funnel portion upon contact with water and/or upon insertion into a tissue such as skin. As used herein, the "funnel" portion may or may not be tapered. That is, the term "funnel" as used herein refers to a portion of the microneedle structure disposed between and connecting the microneedle tip portion and a base portion, e.g., the backing portion of a microneedle patch.

Besides fabricating microneedles, the methods described herein may be applied with a wide range of polymer and drug combinations to fabricate a wide variety of other cast structures, components, and products, including but not limited to other medical devices. Examples of such medical devices include controlled drug delivery devices, such as implantable drug delivery devices, including biodegradable or bioerodible polymer-drug composites. One non-limiting example is devices comprising biodegradable polymers and contraceptive hormones. Those skilled in the art will appreciate that the methods are applicable to many different polymer-drug combinations or other combinations of molecules that have different solubility characteristics to fabricate many other castable devices or other three dimensional objects.

Additional Details

Substance of Interest/Active Pharmaceutical Ingredient

The methods described above can be used with essentially any substance of interest. As used herein, the term "substance of interest" includes active pharmaceutical ingredients, allergens, vitamins, cosmetic agents, cosmeceuticals, diagnostic agents, markers (e.g., colored dyes or radiological dyes or markers), and other materials that are desirable to introduce into a biological tissue. The "substance of interest" is sometimes referred to herein as a drug or an active agent.

In some embodiments, the substance of interest is a prophylactic, therapeutic, or diagnostic agent useful in medical or veterinary application. In some embodiments, the substance of interest is a prophylactic or therapeutic substance, which may be referred to herein as an API. In some embodiments, the API is selected from suitable proteins, peptides and fragments thereof, which can be naturally occurring, synthesized or recombinantly produced. Representative examples of types of API for delivery include antibiotics, antiviral agents, analgesics, anesthetics, antihistamines, anti-inflammatory agents, anti-coagulants, allergens, vitamins, antineoplastic agents.

In some embodiments, the substance of interest is a hormone. The hormone may include a contraceptive hormone, such as a progestin. Examples of contraceptive hormones include levonorgestrel, etonogestrel, and nestorone. The hormone may include glucagon-like peptide-1 (GLP-1). The hormone may include testosterone. The hormone may include an estrogen, e.g., ethinyl estradiol.

In some embodiments, the substance of interest includes a vaccine. Examples of vaccines include vaccines for infectious diseases, therapeutic vaccines for cancers, neurological disorders, allergies, and smoking cessation or other addictions.

The therapeutic agent may be selected from small molecules and larger biotechnology produced or purified molecules (e.g., peptides, proteins, DNA, RNA).

Microneedles, Arrays and Patches

The microneedles may be in an array and configured as a microneedle patch, which may be a combination of a plurality of microneedles extending from a base substrate, or backing, as known in the art. The microneedles can be made of biodegradable, bioerodible, or bioabsorbable polymers (e.g., polylactic acid and poly(lactic-co-glycolic acid)) that may encapsulate a drug, such as a contraceptive hormone (e.g., a progestin, such as levonorgestrel, etonogestrel, or nestorone) for continuous release for at least two weeks, and, in some embodiments, four weeks or longer.

The microneedle arrays include a base substrate and two or more microneedles which extend from a surface of the base substrate. Each microneedle may have a proximal end attached to the base substrate directly, or indirectly via one or more funnel portions, and a distal tip end which is sharp and effective to penetrate biological tissue. The microneedle may have tapered sidewalls between the proximal and distal ends.

Figure 1:
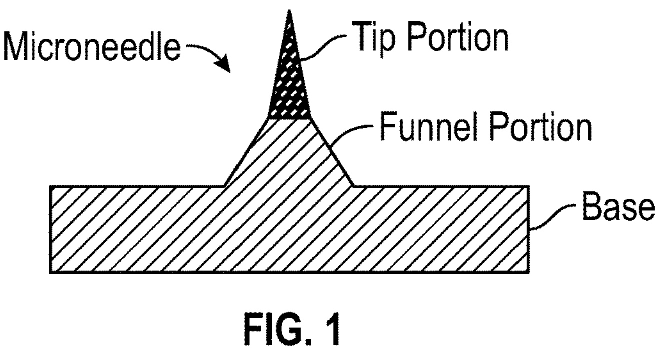
FIG. 1 is a cross-sectional view depicting an embodiment of a microneedle extending from a base or backing of a microneedle patch.

FIG. 1 shows one example of a microneedle in such a microneedle patch. The tip portion here comprises a substance of interest (drug).

The funnel portion may be integrally formed with the microneedle. In some embodiments, the outer surface of the funnel portion can be distinguished from the microneedle portion of the protruding structure by the distinct change/expansion in the angle of the surfaces defining the different portions of the structure, which can be seen as a rapid expansion in at least one dimension (e.g., radially) as one progresses from the distal end toward the proximal end of the microneedle. The funnel portion is wider at its base end than its microneedle end. In some embodiments, the microneedle arrays include an effervescent material dispersed in a funnel portion, the expansion may be designed to permit at least a part of the funnel portion to be inserted into the targeted tissue layer so that a biological fluid, e.g., an interstitial fluid, can contact the funnel portion. In some embodiments, the funnel portion includes none of the substance of interest.

The length of a microneedle ($L_{MN}$) may be between about 50 μm and 2 mm. In most cases they are between about 200 μm and 1200 μm, such as between about 500 μm and 1000 μm. The length (height) of a funnel ($L_{FUN}$) may be between about 10 μm and 1 cm. In most cases, funnels are between about 200 μm and 2000 μm, and more preferably between about 500 μm and 1500 μm. The ratio $L_{FUN}/L_{MN}$ may be between about 0.1 and 10, more typically between about 0.3 and 4 and more preferably between about 0.5 and 2 or between about 0.5 and 1, although a ratio between about 1 and 2 is also useful. The ratio $L_{FUN}/L_{MN}$ could be less than about 1 or could be greater than about 1. The sum $L_{MN}+L_{FUN}$ may be between about 60 um and 1.2 cm, more typically between about 300 um and 1.5 mm and more preferably between about 700 um and 1.2 mm. $L_{MN}+L_{FUN}$ can be greater than about 1 mm, or greater than about 1.2 mm or greater than about 1.5 mm.

The volume of a microneedle ($V_{MN}$) can be between about 1 nl and 100 nl. In most cases, it is between about 5 nl and 20 nl. The volume of a funnel ($V_{FUN}$) can be about 1 nl to 20,000 nl, more typically between about 5 nl and 1000 nl and more preferably between about 10 nl and 200 nl. The ratio $V_{FUN}N_{MN}$ can be between about 0.1 to 100, more typically between about 0.5 and 20 and more preferably between about 1 and 10 or between about 2 and 5.

The microneedle patches may include any one or more of the features and/or configurations described in U.S. Patent Application Publication No. 2017/0050010, which is incorporated herein by reference.

Matrix Materials/Excipients

Matrix materials form the bulk of the microneedles, funnel portions, including the primary funnel portion and secondary funnel portions, and optionally the base substrate. The microneedles, primary funnel portion, and secondary funnel portions may be formed of the same or different matrix materials. The matrix materials typically include a biocompatible polymeric material, alone or in combination with other materials. An effervescent material may be dispersed in the matrix material used to form a funnel portion, a portion of a microneedle, or a combination thereof. A substance of interested may be dispersed in the matrix material used to form microneedles and/or funnel portions.

The matrix materials may be biodegradable, bioerodible, and/or bioabsorbable. One or more matrix materials may be selected based on the rate at which the one or more matrix materials biodegrade, bioerode, or become bioabsorbed. In some embodiments, the matrix materials are water soluble. The water soluble matrix materials may dissolve within minutes to tens of minutes upon contacting a fluid, such as a biological fluid.

In some embodiments, microneedles are formed of a matrix material that is biodegradable, bioerodible, and/or bioabsorbable, and the matrix material encapsulates a substance of interest. The substance of interest is released as the matrix material degrades, erodes, is absorbed, or a combination thereof.

In some embodiments, the bulk of the microneedles are formed from a matrix material including poly-lactic acid, poly-lactic glycolic acid, polycaprolactone, or a combination thereof. In some embodiments, the funnel portions, including the primary funnel portion and/or the secondary funnel portions, are formed from a matrix material include poly-vinyl alcohol, a carbohydrate, or a combination thereof. In some embodiments, the carbohydrate is sucrose. In some embodiments, the funnel portions, including the primary funnel portion and/or the secondary funnel portions, are formed from a matrix material that includes polyvinylpyrrolidone. Other matrix materials, however, are envisioned.

As used herein, the terms "matrix material" and "excipient" are used interchangeably when referring to any excipients that are not volatilized or otherwise removed during drying and formation of the microneedles and funnels.

The fluid solution used in the mold filling processes described herein may include any of a variety of excipients. None, one, or more than one excipient from the following categories of excipients may be used: stabilizers, buffers, bulking agents or fillers, adjuvants, surfactants, disintegrants, antioxidants, solubilizers, lyo-protectants, antimicrobials, antiadherents, colors, lubricants, viscosity enhancer, glidants, and preservatives.

In some preferred embodiments, the microneedle is made of a biodegradable matrix material that encapsulates an API, and upon insertion into a patient the whole microneedle separates and degrades slowly in the skin.

Methods of Making Microneedles

Figure 5:
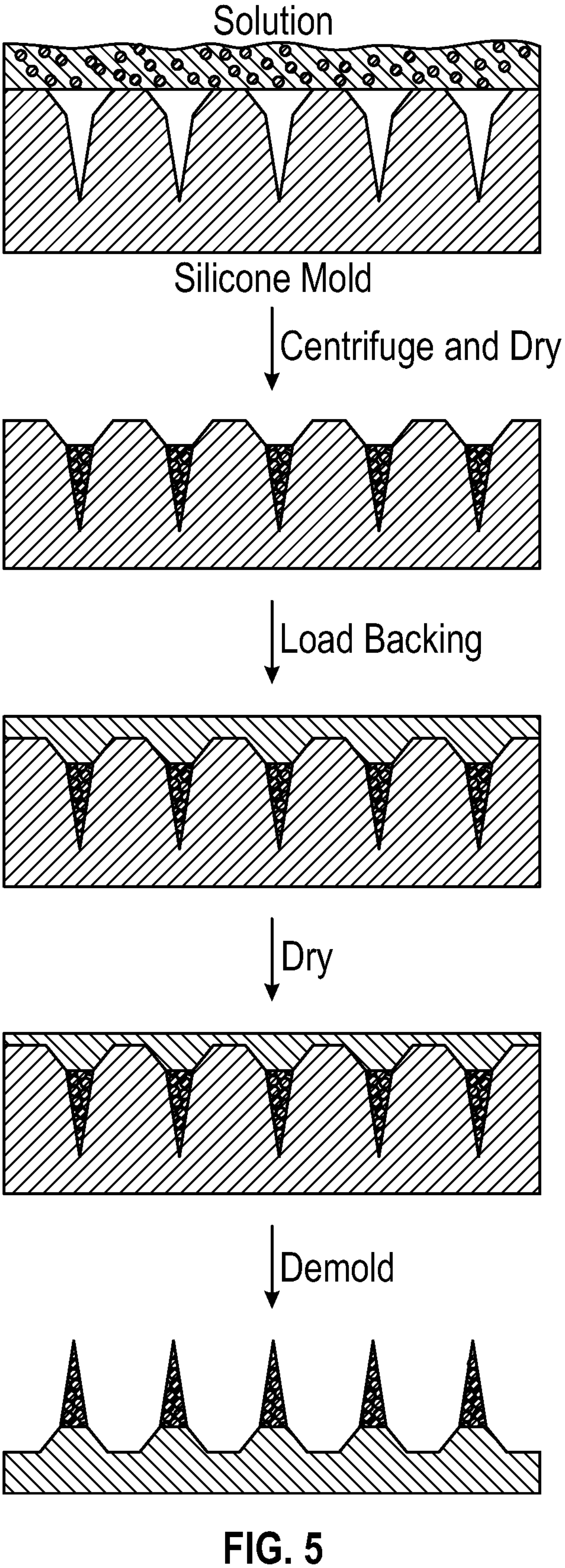
FIG. 5 is schematic illustration of a fabrication process for producing one embodiment of a microneedle patch.

Microneedles or other objects may be made in a molding process that entails providing a suitable mold; filling the mold with suitable fluid materials; drying the fluid materials to form the microneedle tips, filling the mold with suitable matrix materials to cover the tips and form the base substrate; drying the matrix materials; and then removing the formed part from the mold. An example of this is illustrated in FIG. 5. The filling and drying steps may be referred to herein as "casting." The improved casting methods described above are focused on the first steps in which the microneedle tips comprising drug are formed. The method typically includes two or more castings.

The methods described herein may include one or more features, parts, and/or techniques described in or adapted from U.S. Patent Application Publication No. 2017/0050010, and WO 2019/075275, which are incorporated herein by reference.

The composition of the filling solutions generally reflects the desired materials in the final microneedle array, with the exception of the solvents that may be completely or substantially removed during the process.

In some embodiments, the substance of interest is loaded preferentially into the microneedles and their tips, and not into the funnel portions. The substance of interest is part of a filling material that is transferred into the mold. The filling material includes a liquid vehicle. The filling material may be in the form of a solution, slurry or suspension of particles, or a combination of any of these forms. As described above, the filling material preferably includes a colloidal suspension of fine particles, a polymer whose solubility has been reduced to near its point of precipitation from solution, or both. One or more of these forms may be used in a multi-step filling process. This "filling material" may be referred to herein as a "solution" or as a "fluid material".

In various filling steps, the filling material may include a liquid vehicle. The term "liquid vehicle" may be referred to herein as a "solvent" or a "carrier fluid." In various embodiments, the filling material may include (1) only the solvent, (2) no solvent, (3) only a matrix material, (4) a combination of a solvent and a matrix material with no substance of interest, (5) a combination of only a solvent and a substance of interest, or (6) a combination of a solvent, a substance of interest, and a matrix material. The solvent may be water, an organic solvent, such as a volatile organic solvent, or a combination thereof. Some examples are Class 3 solvents that include acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, dimethyl sulfoxide, 2-methyl-1-propanol, ethanol, pentane, ethyl acetate, 1-pentanol, ethyl ether, 1-propanol, ethyl formate, 2-propanol, formic acid, and propyl acetate. Other solvent examples include bis(2-methoxyethyl) ether (diglyme), tetrahydrofuran, dimethylacetamide, dimethylformamide, xylene, dichloromethane, chloroform, hexane, limonene, methylcyclohexane, and combinations thereof. When a microneedle array includes an effervescent material, the liquid vehicle that includes the effervescent material should be a non-aqueous liquid vehicle. The term "non-aqueous", as used herein, refers to liquids that include less than 1% by volume of water.

The microneedle and funnel cavities may be completely filled, partially filled, or overfilled. After a filling step occurs, it is generally followed by a drying or curing step. The drying or curing step can be achieved, for example, by heating and/or a reduction in pressure.

In a preferred embodiment, a two-step filling process is used, wherein the first filling step contains the substance of interest, which substantially migrates into the microneedle and its tip during the drying/curing process. This process is often repeated for another cast of the same material. After the first casting(s) with the substance of interest have been cast and dried, this is followed by a second filling step and a subsequent drying/curing process. This second filling step contains the matrix material(s) that give the microneedles and funnels their mechanical structure and may be overfilled to create the base substrate or part of the base substrate. The second filling step may result in the trapping of an air bubble between the material applied during the first filling step and the material applied during the second filling step.

The molds may be filled with a first solution containing an active (as well as possible excipients), which is then dried. In some cases, the mold is filled again with the same solution and dried. This can be repeated until the desired quantity of active is loaded into the microneedles. This may be followed by one or more final filling steps in which the molds are filled with excipients (which could be the same and or different excipients as in prior fillings) and without active, which provide the microneedles with their mechanical structure once dried.

In some embodiments, a centrifuge or similar device is used to spin the molds, creating a gravitational force to drive the solution down into the microneedles as it dries/cures. This process also can useful be to drive larger molecules (e.g., the active) down into the microneedles and their tips while the filling fluid is still in the solution state. The term "larger molecules" is used to mean molecules that are larger than those of the liquid vehicle, or solvent, and can also include nanoparticles, microparticles and other particles made up of many molecules.

In various embodiments, the microneedle molding process includes one or more of the following steps before, during and/or after any or all of the mold filling steps: application of vibration, ultrasound, pressure, vacuum, an electromagnetic field, and centrifugation.

The volume of solution deposited into the microneedle molds may be controlled by the volume of the cavities within a mold (i.e., completely fill cavity with solution and then clean surface) or the filler (i.e., dispense or load controlled volume, mass, etc.). For microneedle arrays produced by multiple filling steps, these volume control methods may both be used. For example, the solution containing the active is blanket coated over the entire surface, the microneedle and funnel cavities are filled, the solution is cleaned from the surface of the mold, the solution is dried, a second solution is deposited in a controlled amount by a filler, the second solution is dried, etc.

In some embodiments, a fluid handling/dispensing technology/system known in the art to be capable of depositing solutions onto the molds is used. Some are suited for 'blanket' coating (regional or full patch), targeted deposition, or both. The filling heads may be automated and move, the molds may move, or both may move, in order to deposit the solutions in the desired locations. This may be in the form of single-cavity molds, multi-cavity mold plates, or on a continuous reel-to-reel process.

A number of drying and/or curing methods can be used throughout the manufacturing process. Heat may be applied in the form of a batch process, but it may be preferred to be integrated into a semi-batch or continuous process. Some of the drying methods, which harden the solution by removing the solvent via evaporation, include the application of: 1) heat—through convection, conduction (i.e., hot plate or heated surface), and/or radiation (heat lamp, IR or NIR light), 2) convection—dry, desiccated, sterile air or nitrogen blower, 3) vacuum—exposure to reduced pressure, 4) ambient drying, 5) centrifugal force, 6) desiccation, 7) lyophilization or freeze drying, 8) dielectric drying (e.g., RF or microwaves), 9) supercritical drying, and 10) a combination of one or more these drying methods.

As used herein, the term "drying," "dried, or "dry" as it refers to the material in the mold (e.g., the matrix material and/or the substance of interest) refers to the material becoming at least partially solidified. In embodiments, the microneedles may be removed from the mold before being fully dried. In one embodiment, the microneedles are removed from the mold after the microneedles are dried to be an operational state. However, in a preferred embodiment, the microneedles are removed from the mold when the microneedles are in a rubbery state but strong enough to be pulled or peeled out of the mold. This has been found to improve demolding without microneedle breakage. As used herein, the term "operational state" means that the microneedles are sufficiently rigid to be used for their intended purpose, e.g., to penetrate skin. As used herein the term "rubbery state" means that the microneedles are not in an operational state, as they are too soft and flexible to penetrate their intended target tissue, e.g., skin. For example, a microneedle, such as one comprised of a bulk/matrix material including polyvinyl alcohol and a sugar, would, when undergoing a drying process, enter a rubbery state, as its moisture content is reduced, before entering the operational state.

Methods of Using the Microneedle and Arrays

The microneedles, arrays, and patches described herein may be self-administered or administered by another individual. The microneedle patches provided herein may be directly handled and administered by the person applying the patch without requiring use of an applicator to apply the required force/pressure.

In some embodiments, the methods of using the microneedle arrays include a simple and effective method of administering a substance of interest with a microneedle patch. The methods may include identifying an application site and, preferably, sanitizing the area prior to application of the microneedle patch (e.g., using an alcohol wipe). If needed, the application site may be allowed to dry before application of the microneedle patch. The patch then is applied to the patient's skin/tissue and manually pressed into the patient's skin/tissue (e.g., using the thumb or finger) by applying a sufficient pressure to insert the one or more microneedles into the patient's skin/tissue.

In some embodiments, the microneedles will then separate from the microneedle patch upon dissolution of the funnel portion, for example, if the funnel portion includes an effervescent material. When an effervescent material is included in the funnel portion, the microneedles may separate from the microneedle patch within about 10 seconds to about 120 seconds after the microneedle patch is pressed into the patient's skin/tissue. In some embodiments, the microneedles separate from the microneedle about 40 second to about 60 seconds after the microneedle patch is pressed into the patient's skin/tissue.

After separation of the microneedles from the patch, the patch may be removed from the patient's skin/tissue. The patch may be removed by manually grasping and pulling a tab portion (e.g., between the thumb and finger), and discarding the patch. Due to the separation of the microneedles from the patch, the patch may be discarded as non-sharps waste.

In some embodiments, following microneedle separation, the microneedles may dissolve readily (within minutes to tens of minutes). In some embodiments, the microneedles may dissolve, bioerode, biodegrade, and/or be bioabsorbed over days, weeks or months.

In some embodiments, the microneedle patches described herein are used to deliver one or more substances of interest (e.g., vaccines, therapeutics, vitamins) into the body, tissue, cells, and/or organs. In some embodiments, the microneedles are used to deliver the active into skin by inserting the microneedles across the stratum corneum (outer 10 to 20 microns of skin that is the barrier to transdermal transport) and into the viable epidermis and dermis. The microneedles are preferably dissolvable and once in the intradermal space they dissolve within the biological fluid and release the active into the skin. The microneedles can be formulated to release active over extended periods. The extended period may be at least two weeks, at least four weeks, at least six weeks, at least eight weeks, at least three months, at least six months, at least nine months, or at least a year.

Unless otherwise defined herein or below in the remainder of the specification, all technical and scientific terms used herein have meanings commonly understood by those of ordinary skill in the art to which the present disclosure belongs. It is also to be understood that the terminology used herein is for the purpose of describing particular embodiments only, and is not intended to be limiting. In describing and claiming the present embodiments, the following terminology will be used in accordance with the definitions set out below.

The term "about", as used herein, indicates the value of a given quantity can include quantities ranging within 10% of the stated value, or optionally within 5% of the value, or in some embodiments within 1% of the value.

EXAMPLES

The invention may be further understood with reference to the following non-limiting examples.

Example 1—Reduced Polymer Solubility Formulation

Figure 6A:
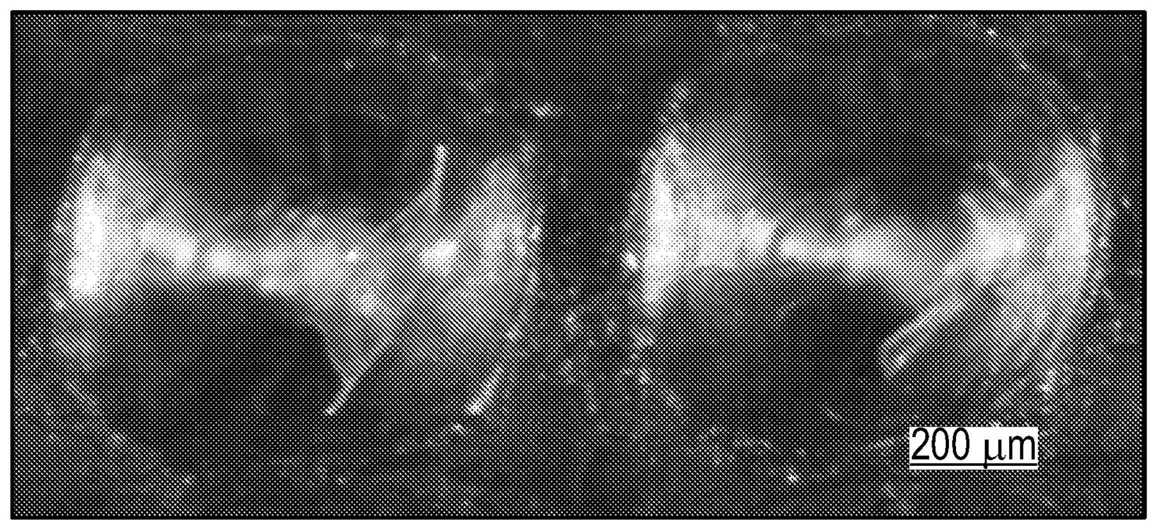
FIGS. 6A-6B are microphotographs showing examples of cast microneedle tips formed in a mold, with above showing film in funnel region left by standard process using a soluble polymer/drug formulation in organic solvent, and below showing the tips cast by the improved methods of the invention using reduced solubility polymer and drug.
Figure 6B:
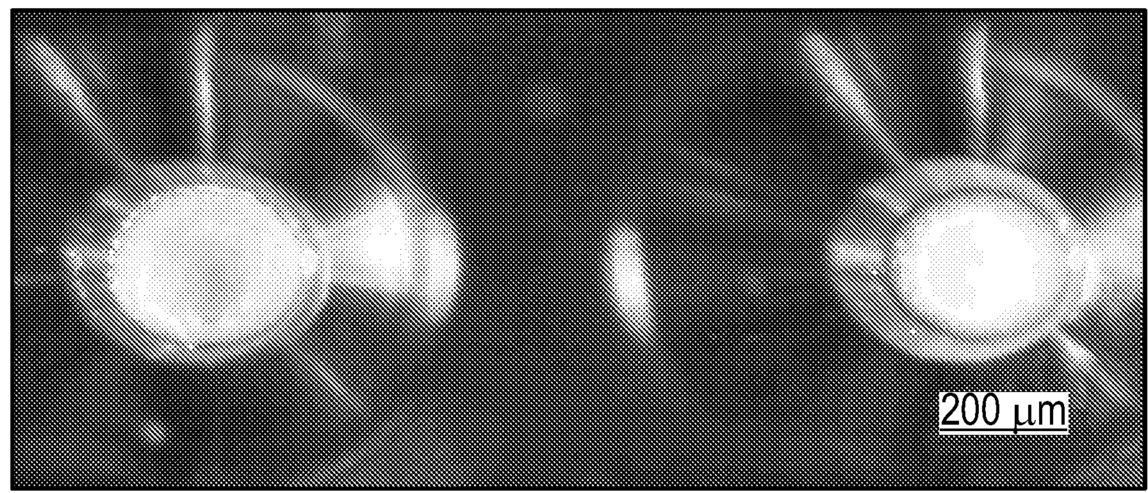

A solution containing 10% poly (D,L-lactide-co-glycolide) (PLGA), 50:50, acid-terminated, in diglyme (DGM) was prepared. An aliquot of 10% PLGA in DGM solution was weighed, and an amount of 5% levonorgestrel (LNG) dissolved in DGM was added that was equivalent to a 50:50 ratio of PLGA to LNG. An amount of dioxane was then added that was equivalent to 20% of the solvent composition of the PLGA/LNG solution. A calculated amount of DGM was then added to adjust the PLGA concentration to 3%. The clear solution was then stirred, and water was added dropwise until the solution became hazy, which is hypothesized to indicate that the polymer conformation had tightened and the PLGA was on the verge of precipitation or just beginning to precipitate. The formulation was then cast onto silicone microneedle molds that were centrifuged at 4200 rpm for 40 minutes at 40° C. to pack the needle tips of the mold with the formulation and evaporate the solvent. The result of this casting was microneedle molds with needle tips packed with 50% LNG/50% PLGA, which had little or no additional film of polymer above the packed tips. This result was achieved without the use of solvent washes that are often required after casting PLGA/drug formulations. FIGS. 6A-6B show a comparison of a microneedle cavity cast from a true solution of LNG/PLGA (FIG. 6A) with the formulation of Example 1 (FIG. 6B). In the upper images, the film in the funnel region of the mold has been peeled away from the mold surface for better visualization. In the lower images, there is little or no visible film in the funnel region, and the LNG and PLGA are mostly or all in the tip region of the mold.

It was later found that initial centrifugation at colder temperatures further reduces the formation of film in the funnel region of the mold, and formulations of Example 1 were centrifuged at 10° C. for 15 minutes before centrifuging for another 30 minutes at 40° C. to further dry the formulation.

Example 2—Reduced Polymer Solubility Formulation

A strong, volatile solvent was used to solubilize a drug into a polymer solution containing water, a non-solvent for the drug and polymer, and a low volatility solvent that is a weak solvent for the drug. The volatile solvent was allowed to evaporate, and this caused the drug to precipitate as a fine colloidal suspension within the polymer solution. When the formulation was cast onto a silicone microneedle mold and dried by centrifugation, it was discovered that the colloidal drug particles more readily filled and packed into the microneedle cavities, producing a much less concave tip fill with a significant reduction in the amount of film adhered to the silicone mold above the tip cavity. This resulted in a higher amount of drug being loaded into the tips of the microneedle patch and a reduction of drug lost during casting.

Example 3—Precipitated Drug Formulation (PDS)

A solution containing 5% poly (D,L-lactide-co-glycolide) (PLGA), 50:50, ester-terminated, in diglyme (DGM) was prepared. An aliquot of 5% PLGA in DGM solution was weighed, and an amount of 5% levonorgestrel (LNG) dissolved in tetrahydrofuran (THF) was added equivalent to a 60:40 ratio of PLGA to LNG. Water was then added slowly dropwise to the stirring solution until a pre-calculated amount equivalent to 8% water based on the total solvent composition had been added. The solution of PLGA and LNG remained clear. The capped vial was then weighed, and the vial was uncapped and allowed to stir open on a stir plate in a hood for two days to allow the THF to evaporate. After two days evaporation, the initially clear solution had become a white suspension of colloidal LNG particles in a PLGA solution in DGM/water. The vial was capped and weighed to determine the total amount of solvent lost to evaporation, and additional DGM and water were added to achieve a PLGA concentration of approximately 4% for casting microneedles. The formulation was then cast onto silicone microneedle molds that were centrifuged at 4200 rpm for 40 minutes at 40° C. to pack the needle tips of the mold with the formulation and evaporate the solvent. The microneedle molds were then washed with 20 μl of 5% $H_2O$ in DGM by centrifugation at 4200 rpm for 30 minutes at 40° C. The formulation was then cast a second time on the molds and dried by centrifugation. The molds were then washed three more times with 5% $H_2O$ in DGM with drying by centrifugation. The resulting microneedle tips were evenly packed with 40% LNG/PLGA, and had no additional film of polymer above the packed tips. The microneedle molds with tips were then oven dried and backed with a standard water soluble backing material by standard microneedle finishing methods.

Example 4—Precipitated Drug Formulation (PDS)

The formulation of Example 3 was repeated three different times, altering the drug loading of the microneedles to 50% LNG, 60% LNG and 70% LNG (with the remainder PLGA). Each of these formulations made high quality microneedles, though it was noted that the microneedle tips of the 70% formulation were brittle and more of this formulation's tips were broken during removal from the molds.

Example 5—Precipitated Drug Formulation (PDS)

The formulation and casting of Example 3 was repeated, except that the centrifugation was performed cold at 10° C. for 15 minutes to improve the packing of the tip, followed by a second centrifugation at 40° C. for 15 minutes to dry the mold. Cold initial centrifugation reduced the need for washing the final tips from three times to only once, significantly shortening the time to make the microneedle tips and producing evenly packed tips with no additional film of the formulation above the tips.

Example 6—PDS Formulation for Etonogestrel

Etonogestrel (ENG) was found to be more soluble and water-tolerant than LNG, and it would not precipitate in the formulation of Example 3. Because of this, a new formulation had to be created to precipitate a colloid of ENG in a biodegradable polymer solution. This required identifying a non-solvent for ENG that was an effective solvent for the polymer. Solubility studies with ENG, PLGA and poly (L-lactide) (PLA) were used to determined that xylene was an ENG non-solvent and a solvent for PLA, but not for PLGA. A solution was then prepared containing 5% PLA, 0.55-0.75 dL/g, ester-terminated, in xylene (XYL). The strong, volatile solvent selected to solubilize ENG into PLA/XYL was dichloromethane (DCM). An aliquot of 5% PLA in XYL solution was weighed, and an amount of 5% ENG dissolved in DCM was added equivalent to a 60:40 ratio of PLA to ENG. A clear solution was formed. The capped vial was then weighed, and the vial was uncapped and allowed to stir open on a stir plate in a hood for 24 hours to allow the DCM to evaporate. After 24 hrs of evaporation, the initially clear solution became a white suspension of colloidal ENG particles in a PLA solution in xylene. The vial was capped and weighed to determine the total amount of solvent lost to evaporation. The mass balance indicated that DCM had been evaporated from the solution. Additional XYL was then added to adjust the concentration of PLA to approximately 4% for casting microneedles. The formulation was used to cast microneedle tips by centrifugation as described in Example 3, except that the wash solvent was 50:50 XYL:DGM, which is a non-solvent for ENG. Completed microneedle patches were then fabricated from silicone molds by casting a water soluble backing of polyvinyl alcohol and sucrose on top of the dried PLA/ENG tips, using standard microneedle fabrication methods.

Example 7—Water-Soluble PDS Formulation

A solution containing 20% polyvinylpyrrolidone (PVP, K90) in ethanol (EOH) was prepared. An aliquot of 20% PVP in EOH solution was weighed, and an amount of 4% levonorgestrel (LNG) dissolved in tetrahydrofuran (THF) was added equivalent to a 60:40 ratio of PVP to LNG. Water was then added slowly dropwise to the stirring solution until a pre-calculated amount equivalent to 27% water based on the total solvent composition had been added. A clear solution was formed. The capped vial was then weighed, and the vial was uncapped and allowed to stir open on a stir plate in a hood for two days to allow the THF to evaporate. After two days evaporation, the initially clear solution had become a white suspension of colloidal LNG particles in a PVP solution in ethanol/water. The vial was capped and weighed to determine the total amount of solvent lost to evaporation, and additional EOH/$H_2O$ was added to achieve a PVP concentration of approximately 5% for casting microneedles. Microneedle patches were then fabricated from the molds by standard methods.

Modifications and variations of the methods and devices described herein will be obvious to those skilled in the art from the foregoing detailed description. Such modifications and variations are intended to come within the scope of the appended claims

We claim:

1. A method for making a microneedle, the method comprising:

preparing a casting solution which comprises at least one organic solvent and a polymer and, optionally, a substance of interest, wherein the polymer and the substance of interest, if present, are fully dissolved in the casting solution;

(i) adding a non-solvent for the polymer to the casting solution, and/or (ii) evaporating at least a portion of the at least one organic solvent, wherein the adding and/or evaporating are effective to reduce the effective molecular volume of the polymer in the casting solution; and then casting the casting solution in a mold for the microneedle, wherein the casting solution that is cast in the mold for the microneedle is the casting solution produced by the step of (i) adding the nonsolvent for the polymer to the casting solution, and/or (ii) evaporating the at least a portion of the at least one organic solvent, wherein the polymer in the casting solution that is cast has a concentration that is within 5% of the solubility limit of the polymer in a solvent system of the casting solution comprising the at least one organic solvent.

2. The method of claim 1, wherein the casting solution comprises a substance of interest, and wherein the adding a non-solvent to the casting solution and/or the evaporating at least a portion of the at least one organic solvent is/are effective to precipitate the substance of interest as a colloid or suspension in the casting solution.

3. The method of claim 1, wherein the casting comprises drying, centrifugation, and/or application of a vacuum to the casting solution in the mold.

4. The method of claim 1, wherein the at least one organic solvent comprises two different organic solvents.

5. The method of claim 1, wherein the mold is formed of silicone or another elastomer.

6. The method of claim 5, wherein the mold comprises a cavity having a microneedle tip portion and a funnel portion.

7. The method of claim 6, wherein the casting solution forms the microneedle tip portion, and the reduction of the effective molecular volume of the polymer is effective to avoid formation of a polymeric film on the funnel portion.

8. The method of claim 1, wherein the casting solution that is cast in the mold for the microneedle is the casting solution produced by the step of (i) adding a non-solvent for the polymer to the casting solution to precipitate the substance of interest as a colloid or suspension in the casting solution.

9. The method of claim 1, wherein the casting solution that is cast in the mold for the microneedle is the casting solution produced by the step of (ii) evaporating at least a portion of the at least one organic solvent to precipitate the substance of interest as a colloid or suspension in the casting solution.

10. The method of claim 1, wherein the casting solution that is cast in the mold for the microneedle is the casting solution produced by the step of (i) adding a non-solvent for the polymer to the casting solution, and (ii) evaporating at least a portion of the at least one organic solvent, to precipitate the substance of interest as a colloid or suspension in the casting solution.

11. The method of claim 1, wherein the polymer in the casting solution that is cast has a concentration that is within 1% to 2% of the solubility limit of the polymer in the solvent system of the casting solution comprising the at least one organic solvent.

12. The method of claim 1, wherein the microneedle is part of a microneedle array.

13. The method of claim 1, wherein the substance of interest is present in the casting solution and comprises a prophylactic or therapeutic agent.

14. The method of claim 13, wherein the polymer is a biodegradable polymer.

15. The method of claim 14, wherein the substance of interest comprises a contraceptive hormone.

16. A method for making a microneedle, the method comprising the following ordered steps:

(i) preparing a casting solution which comprises at least one organic solvent and a polymer and a substance of interest, wherein the polymer is fully dissolved in the at least one organic solvent of the casting solution;

(ii) adding a non-solvent for the polymer to the casting solution in an amount effective to reduce the effective molecular volume of the polymer in the casting solution; and then (iii) casting the casting solution in a mold for the microneedle, wherein the casting solution that is cast in the mold for the microneedle is the casting solution produced by the step of adding the non-solvent for the polymer to the casting solution.

17. The method of claim 16, wherein the mold comprises a cavity having a microneedle tip portion and a funnel portion, and wherein the casting solution forms the microneedle tip portion, and the reduction of the effective molecular volume of the polymer is effective to avoid formation of a polymeric film on the funnel portion.

18. The method of claim 16, wherein the adding the non-solvent for the polymer to the casting solution causes the substance of interest to precipitate as a colloid or suspension in the casting solution.

19. The method of claim 16, wherein the polymer in the casting solution that is cast has a concentration that is within 5% of the solubility limit of the polymer in the solvent system of the casting solution comprising the at least one organic solvent.

20. The method of claim 16, wherein the microneedle is part of a microneedle array.

21. The method of claim 16, wherein the substance of interest comprises a prophylactic or therapeutic agent.

22. The method of claim 21, wherein the polymer is a biodegradable polymer.

23. The method of claim 22, wherein the substance of interest comprises a contraceptive hormone.

24. A method for making a microneedle, the method comprising the following ordered steps:

(i) preparing a casting solution which comprises at least one organic solvent and a polymer and a substance of interest, wherein the polymer is fully dissolved in the at least one organic solvent of the casting solution;

(ii) evaporating at least a portion of the at least one organic solvent in an amount effective to reduce the effective molecular volume of the polymer in the casting solution; and then (iii) casting the casting solution in a mold for the microneedle, wherein the casting solution that is cast in the mold for the microneedle is the casting solution produced by the step of evaporating the at least a portion of the at least one organic solvent, wherein the polymer in the casting solution that is cast has a concentration that is within 5% of the solubility limit of the polymer in the solvent system of the casting solution comprising the at least one organic solvent.

25. A method for making a microneedle, the method comprising the following ordered steps:

(i) preparing a casting solution which comprises at least one organic solvent and a polymer and a substance of interest, wherein the polymer is fully dissolved in the at least one organic solvent of the casting solution;

(ii) evaporating at least a portion of the at least one organic solvent in an amount effective to reduce the effective molecular volume of the polymer in the casting solution; and then (iii) casting the casting solution in a mold for the microneedle, wherein the casting solution that is cast in the mold for the microneedle is the casting solution produced by the step of evaporating the at least a portion of the at least one organic solvent, wherein the evaporating at least a portion of the at least one organic solvent causes the substance of interest to precipitate as a colloid or suspension in the casting solution.

26. The method of claim 25, wherein the mold comprises a cavity having a microneedle tip portion and a funnel portion, and wherein the casting solution forms the microneedle tip portion, and the reduction of the effective molecular volume of the polymer is effective to avoid formation of a polymeric film on the funnel portion.

27. The method of claim 25, wherein the microneedle is part of a microneedle array.

28. The method of claim 25, wherein the substance of interest comprises a prophylactic or therapeutic agent.

29. The method of claim 28, wherein the polymer is a biodegradable polymer.

30. The method of claim 29, wherein the substance of interest comprises a contraceptive hormone.

* * * * *